(12) United States Patent
Hegde

(10) Patent No.: US 6,620,159 B2
(45) Date of Patent: *Sep. 16, 2003

(54) CONDUCTIVE EXPANDABLE ELECTRODE BODY AND METHOD OF MANUFACTURING THE SAME

(75) Inventor: Anant V. Hegde, Newark, CA (US)

(73) Assignee: SciMed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 35 days.

(21) Appl. No.: 09/876,009

(22) Filed: Jun. 6, 2001

(65) Prior Publication Data

US 2002/0188289 A1 Dec. 12, 2002

(51) Int. Cl.[7] .............................................. A61B 18/18
(52) U.S. Cl. ..................................................... 606/41
(58) Field of Search ............................... 607/101, 102, 607/115–116; 604/20, 21, 96–103; 606/27–31, 46–50, 41

(56) References Cited

U.S. PATENT DOCUMENTS

| | | | | |
|---|---|---|---|---|
| 5,277,201 A | * | 1/1994 | Stern | 606/32 |
| 5,471,982 A | | 12/1995 | Edwards et al. | 128/642 |
| 5,499,971 A | * | 3/1996 | Shapland et al. | 604/21 |
| 5,505,730 A | * | 4/1996 | Edwards | 604/21 |
| 5,575,810 A | | 11/1996 | Swanson et al. | 607/99 |
| 5,836,874 A | | 11/1998 | Swanson et al. | 600/374 |
| 5,846,239 A | * | 12/1998 | Swanson et al. | 606/41 |
| 5,868,778 A | * | 2/1999 | Gershony et al. | 604/96.01 |
| 5,925,038 A | * | 7/1999 | Panescu et al. | 606/41 |
| 6,012,457 A | * | 1/2000 | Lesh | 128/898 |
| 6,024,740 A | | 2/2000 | Lesh et al. | 606/34 |
| 6,248,121 B1 | * | 6/2001 | Nobles | 606/194 |
| 6,517,533 B1 | * | 2/2003 | Swaminathan | 606/20 |

* cited by examiner

Primary Examiner—Michael Peffley
Assistant Examiner—Peter J Vrettakos
(74) Attorney, Agent, or Firm—Bingham McCutchen LLP

(57) ABSTRACT

A balloon body of an electrode assembly includes an elastomeric non-conductive body expandable to a wide variety of working diameters to accommodate a wide variety of anatomical structures. The elastomeric non-conductive body has a circumferential region and an interior adapted to receive an electrically conductive fluid medium for expanding the elastomeric non-conductive body and transmitting electrical current therethough. A plurality of holes are located in the circumferential region of the elastomeric non-conductive body and a conductive elastomeric material covers the holes and forms one or more conductive regions adapted to transmit electrical current received from the electrically conductive fluid medium through the plurality of holes to adjacent body tissue.

44 Claims, 3 Drawing Sheets

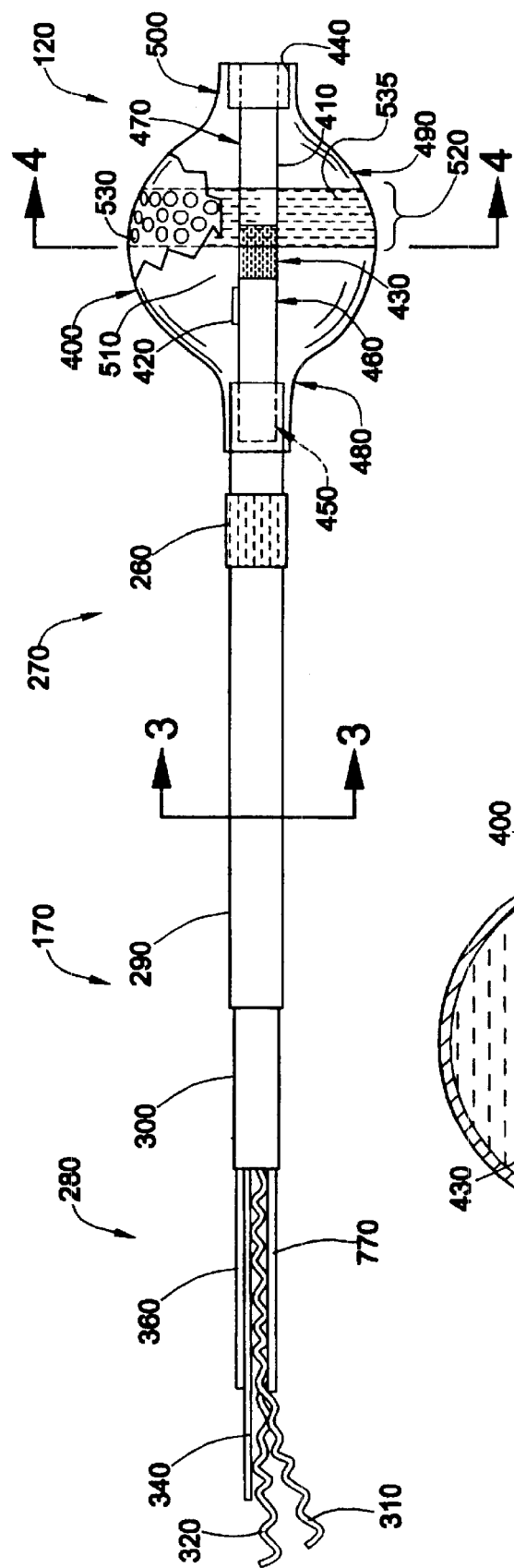
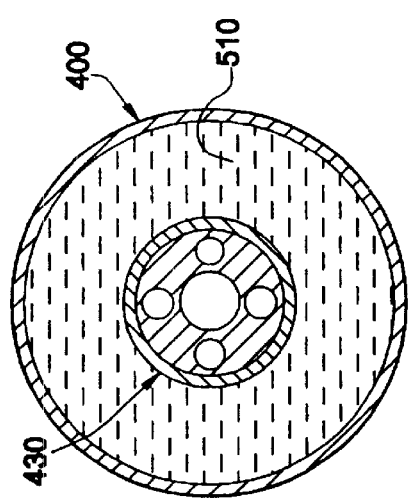
FIG. 2
FIG. 4

CONDUCTIVE EXPANDABLE ELECTRODE BODY AND METHOD OF MANUFACTURING THE SAME

FIELD OF THE INVENTION

The present invention relates, in general, to expandable electrode bodies used in ablating body tissue and methods of manufacturing the same, and, in particular, to expandable electrode bodies for ablating pulmonary vein tissue and related tissue and methods of manufacturing the same.

BACKGROUND OF THE INVENTION

Normal sinus rhythm of the heart begins with the sinoatrial node (or "SA node") generating a depolarization wave front, or electrical impulse. This impulse causes adjacent myocardial tissue cells in the right and left atria to depolarize. The electrical impulse uniformly propagates across the right and left atria and the atrial septum to the atrioventricular node (or "AV node"), causing the atria to contract and empty blood from the atria into the ventricles. The electrical impulse propagates through the AV node to the atrioventricular bundle (or "HIS bundle"), where it further propagates across the ventricles, causing the ventricles to contract. The AV node regulates the propagation delay to the HIS bundle, so that atrial systole occurs during ventricular diastole. This coordination of the electrical activity results in the described, organized sequence of myocardial contraction leading to a normal heartbeat.

Sometimes aberrant conductive pathways develop in heart tissue, which disrupt the normal path of depolarization events. For example, anatomical obstacles, called "conduction blocks," can cause the electrical impulse to degenerate into several circular wavelets that circulate about the obstacles. These wavelets, called "reentry circuits," disrupt the normal activation of the atria or ventricles. As a further example, localized regions of ischemic myocardial tissue may propagate depolarization events slower than normal myocardial tissue. The ischemic region, also called a "slow conduction zone," creates the substrate for errant, circular propagation patterns, called "circus motion." The circus motion also disrupts the normal depolarization patterns, thereby disrupting the normal contraction of the heart tissue.

The aberrant conductive pathways create abnormal, irregular, and sometimes life-threatening heart rhythms, called arrhythmias. An arrhythmia can take place in the atria, for example, as in atrial tachycardia (AT) or atrial flutter (AF). The arrhythmia can also take place in the ventricle, for example, as in ventricular tachycardia (VT). In treating arrhythmias, it is sometimes essential that the location of the sources of the aberrant pathways (called focal arrhythmia substrates) be located. Once located, the focal arrhythmia substrate can be destroyed, or ablated, e.g., by surgical cutting, or the application of heat. In particular, ablation can remove the aberrant conductive pathway, thereby restoring normal myocardial contraction. An example of such an ablation procedure is described in U.S. Pat. No. 5,471,982, issued to Edwards et al.

Alternatively, arrhythmias may be treated by actively interrupting all of the potential pathways for atrial reentry circuits by creating complex lesion patterns on the myocardial tissue. An example of such a procedure is described in U.S. Pat. No. 5,575,810, issued to Swanson et al.

Frequently, a focal arrhythmia substrate resides at the base, or within, one or more pulmonary veins, wherein the atrial tissue extends. The automaticity created by these substrates results in ectopic atrial tachycardia. Although the effect caused by the depolarization wavefront propagating from the pulmonary vein containing the substrate resembles that caused by re-entrant pathways within the atria, the atrial fibrillation is actually caused by a single focal arrhythmia substrate within the pulmonary vein. Arrhythmia substrates residing at the base of, or within, a pulmonary vein may alternatively participate in circuit with the depolarization wavefront propagating around a single vein or within a slow conduction zone residing near or within the vein.

Current techniques of eradicating these substrates include steering a conventional ablation catheter within the target pulmonary vein, mapping this region to pinpoint the substrate, and ablating targeted tissue. However, this is a time consuming and difficult process. Either extensive mapping must be performed within the pulmonary vein to accurately locate the target ablation site, or multiple lesions must be created to, in effect, "carpet bomb" the substrate. Moreover, the substrate may be located deep within the pulmonary vein, thereby making the manipulations required to steer the catheter's distal tip to the target site difficult.

Another technique involves creating circumferential lesions in endocardial and surrounding tissues, e.g., in and around pulmonary veins, in the inferior vena cava, the superior vena cava, and the sinus coronary, to thereby isolate focal arrhythmia substrates. A variety of catheters with electrodes mounted on their distal ends may be used in performing this technique, an especially popular type being balloon catheters. When balloon catheters are used, at least a portion of the surface area of the balloon typically comprises an electrode that performs the ablation.

A drawback of a conventional electrode balloon for creating circumferential lesions in endocardial and surrounding tissues is that different-sized electrode balloons are required for the different-sized veins and arteries. U.S. Pat. No. 6,012,457 to Lesh proposes using an elastic electrode balloon that may be expanded to different-diameter sizes to accommodate different-diameter ablation areas. Lesh separately discloses porous fluid electrodes through which electrically conductive fluid flows out of the balloon. The electrically conductive fluid serves as a conductive medium for transferring RF energy to surrounding body tissue. A problem with porous fluid electrodes if they are used with an elastomeric balloon material is that the pore size in more relaxed areas of the balloon is smaller than the pore size in more expanded areas of the balloon. Therefore, it is very difficult to control the RF energy delivery using such a balloon. Elastomeric materials expand from a weak point or area and stretch to other areas. The pore size in the weak initiation point or area is larger than the pore size in other areas. As a result, flow of conductive fluid through the pores in the initiation area is greater than the flow of conductive fluid in the other areas, causing energy delivery to not be uniform around the circumference of the balloon. The resulting lesion may not be uniform, may not be circumferential, and/or may not be contiguous. Another problem with the ablation elements or electrodes discussed in Lesh is that they do not allow for alternative ablation element configurations to be easily and inexpensively incorporated into a balloon electrode assembly. The metal ablation element discussed in Lesh requires a conductive lead connected to the ablation element on the outer surface of the balloon. This complicates manufacturing of the balloon. Further, if a metal ablation element is used with an elastomeric balloon, the conductive lead may break upon expansion of the balloon.

Accordingly, there is a need for an expandable elastomeric electrode body that can electrically isolate veins by creating circumferential lesions in tissue, such as in endocardial and surrounding tissue, that can be used over a wide range of different-sized veins, and that allows for alternative conductive configurations to be easily and inexpensively incorporated into a balloon electrode assembly.

SUMMARY OF THE INVENTION

An aspect of the invention involves a balloon body of an electrode assembly. The balloon body includes an elastomeric non-conductive body expandable to a wide variety of working diameters to accommodate a wide variety of anatomical structures. The elastomeric non-conductive body has a circumferential region and an interior adapted to receive an electrically conductive fluid medium for expanding the elastomeric non-conductive body and transmitting electrical current therethrough. A plurality of holes are located in the circumferential region of the elastomeric non-conductive body and a conductive elastomeric material covers the holes and forms one or more conductive regions adapted to transmit electrical current received from the electrically conductive fluid medium through the plurality of holes to adjacent body tissue.

Another aspect of the invention involves a method of manufacturing a balloon body of an electrode assembly. The method includes dipping a mold in an elastomeric non-conductive solution so as to form an elastomeric non-conductive body, creating a plurality of holes in a circumferential region of the elastomeric non-conductive body, and covering the holes with a conductive elastomeric material so as to form one or more conductive regions on the elastomeric non-conductive body.

Other and further objects, features, aspects, and advantages of the present inventions will become better understood with the following detailed description of the accompanying drawings.

BRIEF DESCRIPTION OF DRAWINGS

The drawings illustrate both the design and utility of preferred embodiments of the present invention, in which like elements are referred to with common reference numerals.

FIG. 2 is an enlarged side-elevational view of a portion of a catheter body and the expandable electrode assembly with a conductive balloon body illustrated in FIG. 1.

FIG. 4 is an enlarged cross-sectional view of the expandable electrode assembly taken along line 4—4 of FIG. 2.

DETAILED DESCRIPTION OF THE PREFERRED EMBODIMENTS

Figures 1, 3:
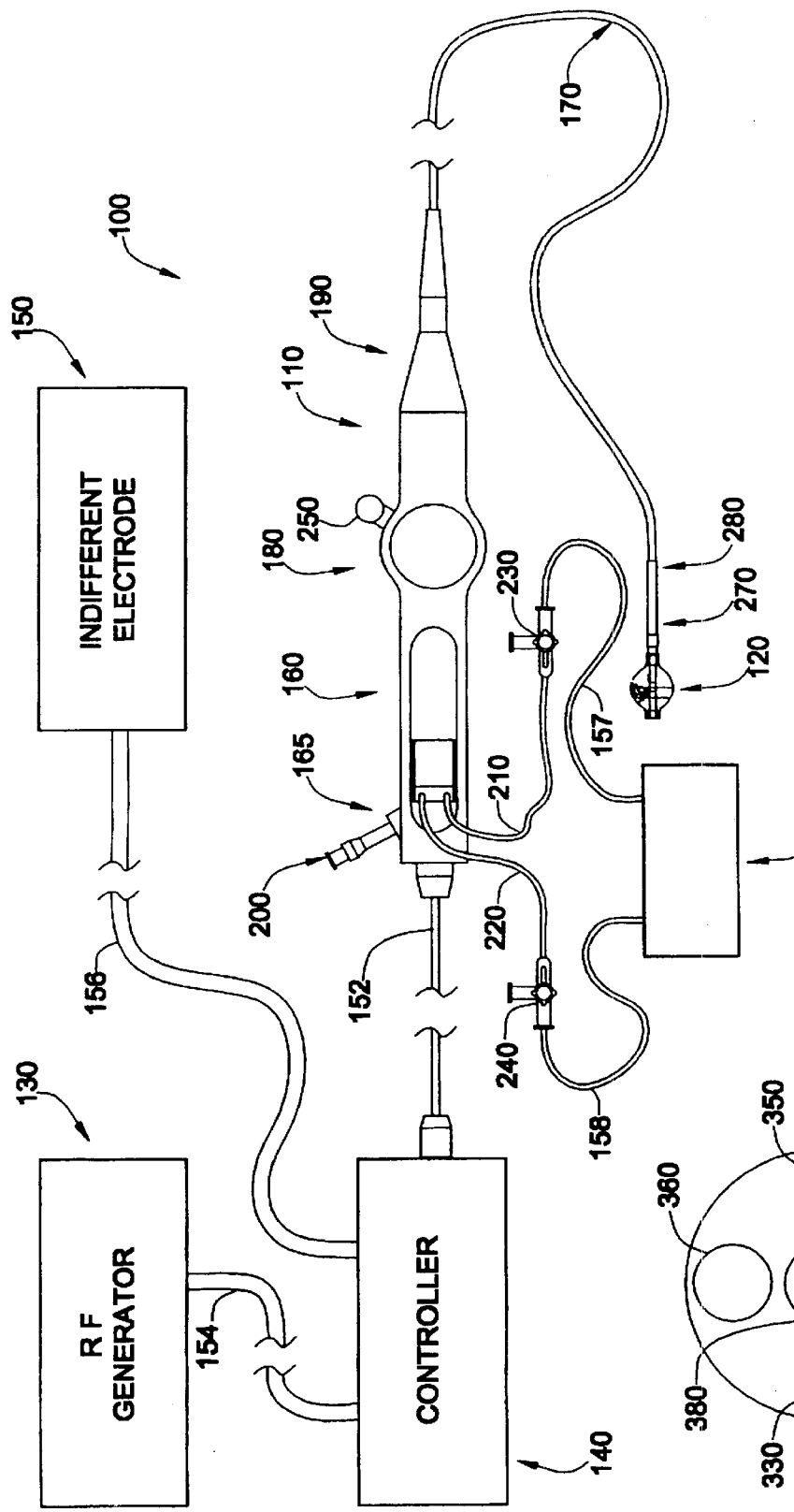
FIG. 1 is a schematic illustration of a RF ablation catheter system including an expandable electrode assembly with a conductive balloon body constructed in accordance with an embodiment of the invention.
FIG. 3 is an enlarged cross-sectional view of the catheter body taken along line 3—3 of FIG. 2.

With reference to FIG. 1, a catheter system 100 including a catheter 110 with an expandable electrode assembly 120 having an elastomeric conductive balloon body constructed in accordance with an embodiment of the invention is shown. In the following description, I) the catheter system 100 will first be generally described, followed by II) a description of the electrode assembly 120, which also includes a description of A) the conductive balloon body, B) a method of manufacturing the conductive balloon body, and C) exemplary alternative embodiments of the conductive balloon body, and III) a description of a method of using the catheter system.

I. Catheter System:

The catheter system 100 includes a RF generator 130, a controller 140, an indifferent electrode 150, a fluid supply 155, and the catheter 110. Each of these will be described in turn.

The RF generator 130 may be any of a variety of well-known RF generators in the art such as, but not by way of limitation, a 150 watt/2 amp RF generator.

The controller 140 may be associated with the RF generator 130, either as an integrated unit or a separate unit, and governs the delivery of RF ablation energy to the expandable electrode assembly 120 according to pre-established criteria. This also allows the catheter 110 to be operated in power control mode. Tissue temperature and/or additional temperatures (e.g., conductive fluid temperature) sensed by one or more temperature sensors (to be described) are processed by the controller 140. Based upon temperature input, the controller 140 may adjust the time and power level of RF energy transmissions by the RF generator 130, in order to achieve desired lesion patterns and other ablation objectives. The controller 140 may include an Automatic Personality Module (APM) that reads the catheter 110 and determines whether the correct catheter is connected to the system 100. In an alternative embodiment, the APM may be separate from the controller 140. The controller 140 may be coupled to the catheter 110 by a catheter cable 152 and the controller 140 may be coupled to RF generator 130 by a connection cable 154.

In a preferred, unipolar arrangement, the indifferent or return electrode 150 is connected to the controller 140 through a connection cable 156. The indifferent electrode 150 is typically an external patch electrode placed upon the patient. RF energy is supplied by the RF generator 130, transmitted circumferentially into surrounding pulmonary vein tissue by the expandable electrode assembly 120, and returned to the indifferent electrode 150. Alternatively, in a bipolar arrangement, the electrode assembly 120 may carry an adjacent, return electrode.

The fluid supply 155 may be connected to the catheter 110 through an inlet tube 157 and an outlet tube 158. The fluid supply 155 includes a reservoir with an electrically conductive medium. The composition of the electrically conductive liquid medium can vary. Preferably, the selected liquid medium possesses a low resistivity to decrease ohmic losses, and thus ohmic heating effects, within the electrode assembly 120. By way of one preferred example, the liquid medium may comprise a hypertonic saline solution, having a sodium chloride concentration at or near saturation, which is about 10% weight by volume. Hypertonic 10% saline solution has low resistivity of only about 5 ohm-cm, compared to blood resistivity of about 150 ohm-cm and myocardial tissue resistivity of about 500 ohm-cm. The electrically conductive liquid medium is conveyed with positive pressure to the interior of the electrode assembly 120, thereby allowing the electrode assembly 120 to assume an expanded geometry. To this end, the fluid supply 155 may include a pump, syringe, or the like to impart this positive pressure and to withdraw the liquid medium from the electrode assembly 120. The electrically conductive liquid medium establishes an electrically conductive path within the electrode assembly 120. In addition to controlling the inflation size of the electrode assembly 120, and serving as a conductive path for ions, the liquid medium may be used to control the temperature of the electrode assembly 120, controlling characteristics of created lesions. A cooling effect can be accomplished in the electrode assembly 120 by continuously or intermittently recycling the inflation medium within the electrode assembly 120. Such use of active cooling allows the electrode assembly 120 to form deep lesions while transmitting ablation energy. To this end, the inflation medium may be recycled at room temperature or may be chilled by an associated chiller (not shown).

The catheter 110 includes a handle 160, a catheter body or shaft 170, and the balloon electrode structure 120, each of which will be described in turn.

The catheter handle 160 includes a proximal portion 165, an intermediate portion 180, and a distal portion 190. The proximal portion 165 carries a through-lumen port 200, an inlet fluid tube or lumen 210, an outlet fluid tube or lumen 220, and the catheter cable 152. The through-lumen port 200 may receive a guide wire for delivering the electrode assembly 120 to the targeted ablation site and/or contrast medium for viewing the electrode assembly 120 within the patient's body. The through-lumen port 200 may also receive a diagnostic catheter such as, but not by way of limitation, the Cardima Pathfinder Mini™ sold by Cardima, Inc. of Fremont, Calif. or any other therapeutic catheters. The catheter cable 152 extends from the proximal portion 165 and carries RF wire(s) 310 (FIG. 2) and temperature sensor wire(s) 320 (which is/are preferably shielded to block RF interference emitted by the RF wire(s) 310). The inlet fluid lumen 210 and the outlet fluid lumen 220 may include respective connectors 230, 240 for connecting the lumens 210, 220 with the tubes 157, 158. The intermediate portion 180 carries an external steering knob or lever 250 of a catheter steering mechanism for manipulating the electrode assembly 120 to create contact with the desired ablation tissue and/or transport the electrode assembly 120 through the vasculature and heart. A rotating cam wheel may be coupled to the external steering lever 250. The cam wheel may be attached to a proximal end of a steering wire 340 (FIG. 2). The steering wire 340 may extend through the catheter body 170 and connect at its distal end to a pull wire anchor 260 secured to a distal portion 270 of the catheter body 170. In operation, rearward movement of the steering lever 250 bends or curves the distal portion 270 of the catheter body 170. In another embodiment, the steering mechanism may include a pair of steering wires that allow for bi-directional steering of the distal portion 270. At the distal portion 190, the catheter body 170 is coupled to the handle 160 via a strain relief.

With reference additionally to FIG. 2, the catheter body 170 includes the distal shaft portion 270 and a proximal shaft portion 280. The catheter body 170 is preferably made of a polymeric, electrically non-conductive material such as, but not limited to, multi-lumen polyvinyl flex tubing 290 that has a draw down into a braid shaft 300. The catheter body may be made of other polymeric, electrically non-conductive materials such as, but not limited to, polyethylene, nylon, polyurethane, and PEBAX® (i.e., polyether block amide).

With reference additionally to FIG. 3, RF wire 310 and temperature sensor wire 320 run through an electrical wire lumen 330 of the tubing 290. Pull or steering wire 340 runs through a pull wire lumen 350. The multi-lumen tubing 290 also includes an inlet or inflation lumen 360 that communicates with, or is the same as, the inlet lumen 210 at the proximal portion 165 of the handle 160, an outlet or exhaust lumen 370 that communicates with, or is the same as, the outlet lumen 220, and a central lumen 380 that communicates with the through-lumen port 200 at the proximal portion 165 of the handle 160.

II Electrode Assembly:

With reference to FIGS. 2 and 4, the expandable electrode assembly 120 will now be described in more detail. The electrode assembly 120 includes an elastic balloon body 400, a distal tube insert 410, a temperature sensor 420, an active ring electrode 430, and a distal balloon mount 440.

The distal tube insert 410 includes a proximal portion 450, an intermediate portion 460, and a distal portion 470. The distal tube insert 410 provides axial support to the balloon body 400 during manipulation of the catheter 110.

The elastic balloon body 400 includes a proximal neck portion 480, an intermediate portion 490, and a distal tip portion 500. The proximal portion 450 of the tube insert 410 may be bonded into, and the neck portion 480 of the balloon body 400 may be bonded onto, the distal portion 270 of the catheter body 170 using cyanoacrylate, UV adhesive, RTV type of adhesive, or epoxy. The distal mount 440 may be bonded onto the distal portion 470 of the tube insert 410 and the tip portion 500 of the balloon body 400 may be bonded onto the distal mount 440 in a similar manner. The distal balloon mount (or another part of the electrode assembly 120 or distal portion 290 of the catheter body 170) may include a radiopaque marker so that the physician can guide the device under fluoroscopy to the targeted site.

The active ring electrode 430 is connected to the RF wire 310 and may be bonded onto the intermediate portion 460 of the tube insert 410. The ring electrode 430 is located within an interior region 510 of the balloon body 400. The ring electrode 430 transmits RF energy that is delivered to pulmonary vein tissue via ionic transport through the conductive inflation medium and conductive region(s) 520 of the balloon body 400 in a manner to be described. In this regard, the ring electrode 430 is preferably made of a material having both a relatively high electrical conductivity and a relatively high thermal conductivity, e.g., gold, platinum, or platinum/iridium.

It should be noted that the ring-like structure of the electrode 430 provides a relatively large circumferential exterior surface in communication with the conductive inflation medium in the interior region 510 of the balloon body 400, providing an efficient means of energizing the inflation medium. Although the electrode 430 is described as a ring, the electrode 430 can take the form of any suitable structure that can contact the inflation medium. The length of the electrode 430 can be accordingly varied to increase or decrease the amount of RF energy delivered to the inflation medium. The location of the electrode 430 can also be varied.

Proximal to the active ring electrode 430, the temperature sensor 420 may be connected to the temperature sensor wire 320 and bonded to the intermediate portion 460 of the tube insert 410. By way of example, the temperature sensor 420 may be a thermistor or thermocouple. The temperature sensor 420 may be located at a different location than that shown in FIG. 2 and/or the electrode assembly 120 may include one or more additional temperature sensors 420 for sensing other temperatures (e.g., tissue temperature) related to the ablation procedure. For example, a temperature sensor may be attached to an interior surface of the balloon body 400 and/or attached to an exterior surface of the balloon body 108 beneath a conductive elastomeric layer to be described. If placed on the balloon body 108, the temperature sensor(s) are preferably placed along the edges of the conductive elastomeric layer, where it adjoins the electrically non-conductive region of the balloon body, where high current densities can occur that lead to higher temperatures at the edges than elsewhere on the conductive elastomeric layer. Placing temperature sensors along the edges assures that the hottest temperature conditions are sensed.

Further details concerning the preferred use of temperature sensors and the placement thereof on an electrode assembly are disclosed and described in U.S. application Ser. No. 08/630,719, which is incorporated by reference as though set forth in full. Further details concerning the use of multiple temperature sensors, including edge temperature sensing elements, and the use of temperature prediction methodologies, are disclosed and described in co-pending U.S. patent application Ser. No. 08/439,824, filed May 12, 1995, which is incorporated by reference as though set forth in full.

A. Conductive Balloon Body:

The elastic balloon body 400 will now be described in more detail. The body 400 is preferably an elastomeric balloon with one or more lesion-creating conductive regions. The balloon body 400 is made of a suitable elastomeric, bio-compatible polymer, such as silicone. Other suitable polymers that may be used include, but not by way of limitation, Santoprene, polyurethane, C-flex, Kraton, latex, and neoprene. The geometry of the balloon body 400 can be altered from a collapsed, low-profile geometry to a wide variety of working diameters to accommodate a wide variety of anatomical structures. When in the low-profile geometry, the balloon body 400 is easily tracked through a small diameter sheath, such as 11 F sheath.

Figures 5C, 5D:
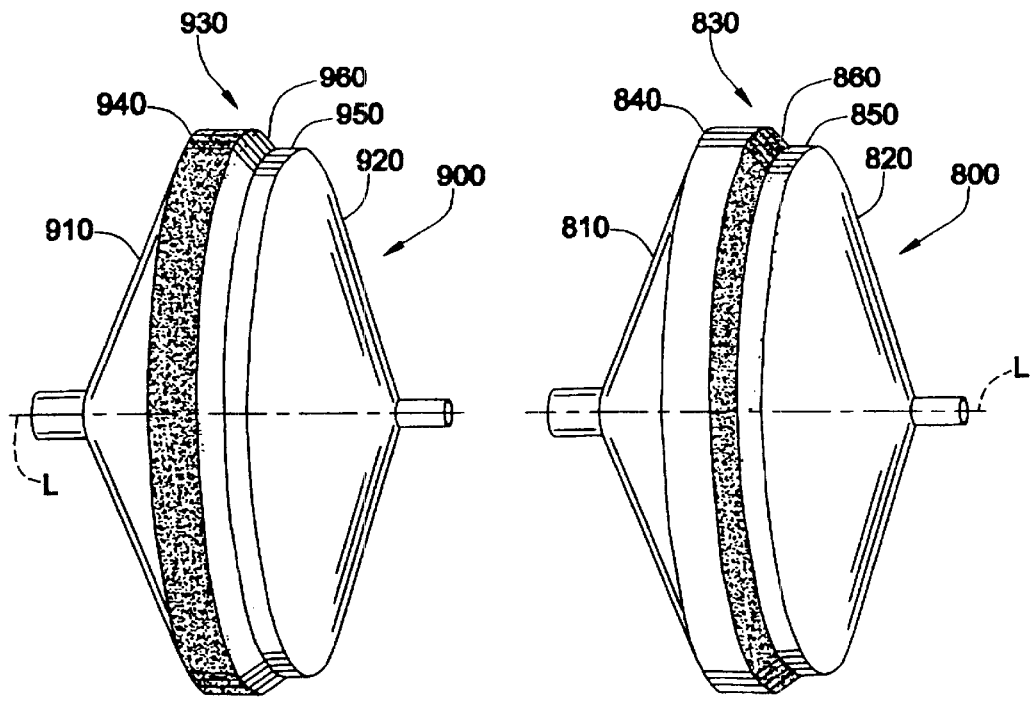
FIGS. 5A–5D illustrate alternative embodiments of the conductive balloon body of the expandable electrode assembly.
Figures 5A, 5B:
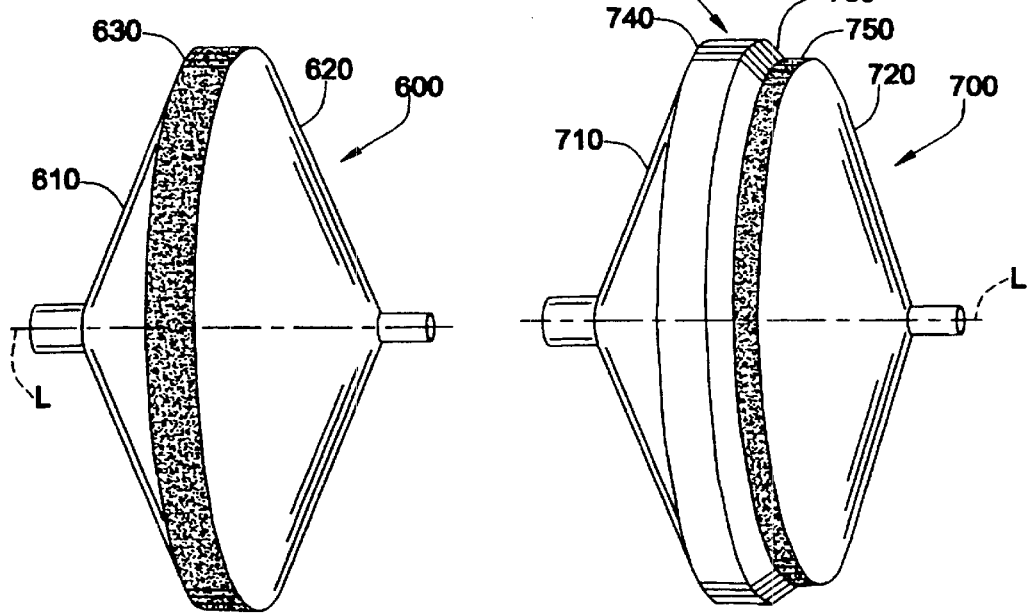

The electrode balloon body 400 can be configured to have any one of many shapes in its expanded geometry depending on the desired resulting geometry. Preferably, the balloon body 400 has a pronounced equatorial region or pronounced circumferential region near its major diameter. In this manner, expansion of the body 400 within the pulmonary vein provides a force that is concentrated between the enlarged circumferential region and the interior surface of a pulmonary vein in which the electrode body 400 is situated, thus enhancing the lesion creating characteristics of the electrode assembly 120, which will be described in further detail below. It should be noted that the configuration of the balloon body 400, the configuration of the circumferential region, the location of an enlarged circumferential portion, etc., may be varied in alternate preferred embodiments. For example, with reference to FIG. 5A, the electrode body may have a "spinning top" configuration with an exaggerated, large-diameter central circumferential region. With reference to FIGS. 5B–5D, the electrode body may have a configuration generally similar to FIG. 5A, but with a stepped diameter central circumferential region. Each of these embodiments will be described in more detail further below.

In a circumferential region 520 of the balloon body 400, a plurality of small holes 530 (e.g., about 0.05 in. diameter) are located in the balloon body 400. A conductive elastomeric material 535 having a relatively high electrical and thermal conductivity is suitably deposited on the outer surface of the balloon body 400 over and in the small holes 530, causing the circumferential region 520 to be a single, continuous, ring-shaped conductive region. In a preferred embodiment, the conductive elastomeric material 535 is Nusil conductive silicone R-2637. In alternative embodiments, other conductive elastomeric materials may be used. Conductive material 535 may be silicone doped with silver or gold flakes.

As will be appreciated by those skilled in the art, the conductive elastomeric material 535 serves as the transmitter of energy that ablates tissue. While the type of ablation energy used can vary, in the illustrated preferred embodiment, the conductive elastomeric material 535 serves to transmit radio frequency (RF) electromagnetic energy. Notably, the conductive elastomeric material 535 is preferably sufficiently flexible to conform to the similar range of geometries (i.e., between collapsed to expanded) as the rest of the electrode body 400.

The conductive elastomeric material 535 need not form a continuous electrically conductive circumferential ring as shown, but may alternatively be segmented—i.e., wherein the conductive material 535 is broken into a plurality of circumferentially displaced conductive segments. In accordance with this alternate arrangement, the underlying holes or pores 530 may be segmented in a like manner. The spacing between the conductive segments is preferably sufficiently close to provide additive heating effects when ablating energy is delivered simultaneously to adjacent segments. Segmenting the conductive circumferential region 520 provides an additional advantage of allowing the electrode balloon body 400 to circumferentially fold upon itself in a consistent, uniform fashion and also allows the conductive region to expand to a larger ratio like the rest of the balloon body 400. The conductive elastomeric material 535 and/or underlying pores 530 may have alternative configurations to form one or more alternatively-shaped conductive regions, depending on the desired lesion pattern to be created and/or treatment area of the body.

B. Method of Manufacturing Conductive Balloon Body:

A preferred method of manufacturing the balloon body 200 will now be described. Wax molds in the shape of the expanded body 200 are dipped in a non-conductive silicone solution and left at room temperature for about twelve hours for the material to set. Then, the coated wax molds are placed in an oven at about 40° to 450° C. for about two hours. Coated molds are removed from the oven and cooled down to room temperature. Holes 530 about 0.05 in. in diameter are created in the balloon body material in the major diameter circumferential region 520. Conductive silicone 530 is dispensed in a desired pattern over the holes 530, plugging the holes 530. Preferably, the pattern of holes 530 and the conductive silicone 530 may form other patterns such as, but not limited to, circumferential segments. The coated molds are left at room temperature for about four hours for the conductive silicone 530 to set. Then, the coated molds are placed in a water bath kept at about 85° C. The wax molds are dissolved and removed, leaving the balloon bodies 400. The balloon bodies 400 are rinsed with room temperature water and placed on a drying rack. The drying rack with the balloon bodies 400 is placed in an oven kept at about 150° C. for about thirty minutes. Then, the rack is removed from the oven and the balloon bodies 400 are cooled down to room temperature.

C. Alternative Embodiments of Conductive Balloon Body:

With reference to FIG. 5A, a balloon body 600 constructed in accordance with another embodiment of the invention will now be described. The configuration of the balloon body 600 is generally similar to that of a "spinning top". The body 600 includes a funnel-shaped or cone-shaped proximal body portion 610 and a symmetric, oppositely oriented funnel-shaped or cone-shaped distal body portion 620 connected by a major-diameter central circumferential conductive region 630 similar to the circumferential conductive region 520 described above. The balloon body 600 is also preferably made of the same materials as the balloon body 400 described above.

With reference to FIGS. 5B–5D, balloon bodies 700, 800, 900 constructed in accordance with further embodiments of the invention will be described. All three balloon bodies 700, 800, 900 include a funnel-shaped or cone-shaped proximal body portion 710, 810, 910 and an oppositely oriented funnel-shaped or cone-shaped distal body portion 720, 820, 920 connected by a stepped-diameter central circumferential region 730, 830, 930 that varies in diameter along its axial length. The stepped-diameter central circumferential region 730, 830, 930 includes a major-diameter central circumferential portion 740, 840, 940 and a distal circumferential portion 750, 850, 950 connected by a circumferential tapered portion 760, 860, 960. The major-diameter central circumferential portion 740, 840, 940 is wider than the distal circumferential portion 750, 850, 950. The balloon bodies 700, 800, 900 are different in that the balloon body 700 illustrated in FIG. 5B has a conductive region in the distal circumferential portion 750, the balloon body 800 illustrated in FIG. 5C has a conductive region in the circumferential tapered portion 860, and the balloon body 900 illustrated in FIG. 5D has a conductive region in the major-diameter central circumferential portion 940.

The stepped-down configuration of the balloon bodies 700, 800, 900 (e.g., cone-shaped distal body portion 720, 820, 920, smaller-diameter distal circumferential portion 750, 850, 950, and tapered circumferential portion 760, 860, 960) allows the user to position the balloon bodies 700, 800, 900 at the mouth of a tapered vascular or venous structure, for example, at the ostium of a pulmonary vein. Providing conductive regions at the distal circumferential portion 750, tapered circumferential portion 860, and/or major diameter central circumferential portion 960 allows the user to create narrow lesions in specific sections of the anatomical structure. The stepped balloon electrode bodies 700, 800, 900 illustrated in FIGS. 5A–5B can be employed to isolate focal arrhythmia substrates in vessels such as the pulmonary vein by creating a circumferential lesion either at the base of the vessel or inside of the vessel, depending on which portion of the stepped balloon electrode body 700, 800, 900 is used. For example, the stepped balloon electrode bodies 700, 800 are more ideal for creating a circumferential lesion at the mouth of the pulmonary vein, while the stepped balloon electrode body 900 is more ideal for creating a circumferential lesion inside of the vessel.

III. Method of Use:

As will now be described, in accordance with a general aspect of the present invention, the catheter system 100 including the electrode assembly 120 with the elastomeric balloon body 400 can be employed to isolate focal arrhythmia substrates in a pulmonary vein by creating a circumferential lesion inside of the pulmonary vein.

Using a conventional introducer guide sheath, a guide wire, or just the catheter 110, a physician can direct the electrode assembly 120 into the left atrium of the patient, while the electrode balloon body 400 is in its low profile (i.e., deflated) geometry. This can be accomplished via a conventional retrograde approach through the respective aortic and mitral valves of the heart. Alternatively, a transseptal approach can be employed to direct the electrode assembly 120 into the right atrium through the atrial septum and into the left atrium. A detailed description of methods for introducing a catheter into the left atrium via a transeptal approach is disclosed in U.S. Pat. No. 5,575,810, issued to Swanson et al., which is fully incorporated herein by reference.

Once inside the left atrium, the physician can deliver the electrode assembly 120 into a desired pulmonary vein by employing the steering lever 250 on the handle 160 of the catheter 110. Alternatively, the guide sheath or guide wire used to deliver the electrode assembly 120 into the left atrium can be situated in the desired pulmonary vein for delivery of the electrode assembly 120 therein.

In order to isolate focal arrhythmia substrates located in a pulmonary vein, the physician situates the electrode balloon body 400 into the pulmonary vein such that the enlarged circumferential region 520 is disposed in a selected tissue region in the interior of the pulmonary vein, adjacent to the opening into the left atrium. Once the electrode assembly 120 is properly situated within the pulmonary vein, the physician causes the balloon body 400 to take its expanded geometry via the injection or transfer of the pressurized liquid medium from the fluid supply 155 through the inflation tube(s) and lumen 360. The liquid medium fills the interior 510 of the balloon body 400 and exerts pressure on the inside of the balloon body 400, urging it from a collapsed geometry to an expanded geometry. Constant exertion of pressure maintains the balloon body 400 in its expanded state. As indicated above, the electrically conductive liquid medium may be continuously or intermittently circulated through the balloon body 400 to maintain the balloon body 400 in its expanded state and cool the balloon body 400. The balloon body 400 is preferably inflated to a degree that places the conductive circumferential region 520 into firm contact with the selected tissue region of the pulmonary vein.

The physician then conveys RF energy from the generator 130 to the interior ring electrode 420, as governed by the controller 140, whereby RF currents are carried by the ions in the electrically conductive fluid medium, through the pores 530 to the conductive elastomeric material 535. The RF energy is applied to the surrounding tissue in a pattern corresponding to the pattern of the elastomeric material 535 on the balloon body 400. The RF energy is transmitted into the surrounding body tissue to the return electrode 150, thereby forming a unipolar arrangement. The transmitted RF energy creates a lesion covering a circumferential region of the pulmonary vein proximate the conductive elastomeric material 535, whereby the lesion isolates the focal arrhythmia substrates from the left atrium, restoring normal myocardial contraction.

Following the ablation process, the physician causes the electrode balloon body 400 to return to its collapsed geometry—i.e., by removing the liquid inflation medium from the interior 520 of the body 400 through the exhaust lumen 370. The physician can then extract the electrode assembly 120 from the pulmonary vein, after which it can be repositioned inside another pulmonary vein for continued ablation therapy or extracted altogether from the patient.

If the conductive elastomeric material 535 is circumferentially segmented, after a first round of ablation, resulting lesions will extend over only portions of the vessel adjacent the conductive elastomeric material segments. Because it is preferred that the lesions form a continuous ring, these remaining areas are then ablated by slightly rotating the entire catheter and ablating any remaining tissue one or more additional times as needed.

In a like manner, the stepped-diameter balloon bodies 700, 800, 900 illustrated in FIGS. 5B, 5C, 5D may be used to ablate vascular tissue, preferably to create narrow lesions in specific sections near a mouth or base of a tapered vascular or venous structure, for example, at the ostium of a pulmonary vein. The physician may simply select a stepped-diameter balloon body 700, 800, 900 with a circumferential conductive region most appropriate for the targeted vascular region and follow the process described above.

Although the above-described preferred method has been directed to the creation of lesions in pulmonary veins and surrounding openings of the left atrium of the heart, the system, method, assembly, and body disclosed and described herein can be used to perform tissue ablation procedures in and around the Inferior Vena Cava, the Superior Vena Cava, left and right ventricles, the free wall of the atria, and the Sinus Coronary, which are located in the right atrium, as well as other vessels and cavities within the body, e.g., the esophagus in treating gastroesophageal reflux disease, and other body tissue.

The conductive balloon body is advantageous in that the elastomeric non-conductive body and conductive elastomeric material forming the conductive region(s) are readily expandable to a wide variety of working diameters to accommodate a wide variety of anatomical structures for tissue ablation purposes. Further, providing holes in the elastomeric non-conductive body with a conductive elastomeric material thereon allows one or more conductive elastomeric regions in any desired configuration to be easily and inexpensively formed on the elastomeric non-conductive body. Because there are no conductive leads to the conductive region(s), manufacturing is simpler and the elastomeric balloon body is free to expand without any concern of lead wire breakage. Also, because the conductive region(s) are not porous fluid electrodes, the above-described problems with controlling RF energy delivery using such electrodes are eliminated.

While preferred embodiments and methods have been shown and described, it will be apparent to one of ordinary skill in the art that numerous alterations may be made without departing from the spirit or scope of the invention. Therefore, the invention is not to be limited except in accordance with the following claims.

We claim:

1. A balloon body of an electrode assembly, comprising:
   an elastomeric electrically non-conductive body expandable to a wide variety of working diameters to accommodate a wide variety of anatomical structures, the elastomeric non-conductive body including a circumferential region and an interior adapted to receive an electrically conductive fluid medium for expanding the elastomeric non-conductive body and transmitting electrical current therethrough;
   a plurality of holes located in the circumferential region of the elastomeric non-conductive body; and
   an electrically conductive non-porous elastomeric material covering the holes and forming one or more electrically conductive regions adapted to transmit electrical current received from the electrically conductive fluid medium through the plurality of holes to adjacent body tissue.

2. The balloon body of claim 1, wherein the conductive elastomeric material forms a continuous ring-shaped conductive region in the circumferential region of the elastomeric non-conductive body.

3. The balloon body of claim 1, wherein the conductive elastomeric material forms multiple segmented conductive regions in the shape of a ring in the circumferential region of the elastomeric non-conductive body.

4. The balloon body of claim 1, wherein the conductive elastomeric material plugs the holes in the circumferential region of the elastomeric non-conductive body.

5. The balloon body of claim 1, wherein the elastomeric non-conductive body is made of silicone.

6. The balloon body of claim 1, wherein the conductive elastomeric material is conductive silicone.

7. The balloon body of claim 1, wherein the holes are about 0.05 in. in diameter.

8. The balloon body of claim 1, wherein the elastomeric non-conductive body includes a generally "spinning top" configuration.

9. The balloon body of claim 1, wherein the elastomeric non-conductive body includes a generally funnel-shaped proximal portion and a symmetric, oppositely oriented, generally funnel-shaped distal portion connected by the circumferential region.

10. The balloon body of claim 1, wherein the circumferential region has a stepped-diameter configuration with a major-diameter central circumferential portion, a circumferential tapered portion, and a distal circumferential portion.

11. The balloon body of claim 10, wherein the one or more conductive regions is located in the major-diameter central circumferential portion.

12. The balloon body of claim 10, wherein the one or more conductive regions is located in the circumferential tapered portion.

13. The balloon body of claim 10, wherein the one or more conductive regions is located in the distal circumferential portion.

14. The balloon body of claim 1, wherein the balloon body includes one or more temperature sensors.

15. The balloon body of claim 1, further including an internal electrode located in the interior and adapted to transmit electrical current to the electrically conductive fluid medium.

16. The balloon body of claim 14, wherein the body includes a balloon wall that carries the one or more temperature sensors.

17. The balloon body of claim 1, wherein the conductive elastomeric material covers substantially all of the holes located in the circumferential region of the elastomeric non-conductive body.

18. The balloon body of claim 1, wherein the one or more conductive regions are ablative.

19. A balloon body of an electrode assembly, comprising:
   an elastomeric electrically non-conductive body expandable to a wide variety of working diameters to accommodate a wide variety of anatomical structures, the elastomeric non-conductive body including a circumferential region and an interior adapted to receive an electrically conductive fluid medium for expanding the elastomeric non-conductive body and transmitting electrical current therethrough;
   a plurality of holes located in the circumferential region of the elastomeric non-conductive body; and
   an electrically conductive elastomeric layer comprising a metallic substance, the conductive layer covering the holes and forming one or more electrically conductive regions adapted to transmit electrical current received from the electrically conductive fluid medium through the plurality of holes to adjacent body tissue.

20. The balloon body of claim 19, wherein the conductive elastomeric layer forms multiple segmented conductive region in the shape of a ring in a circumferential region of the elastomeric non-conductive body.

21. The balloon body of claim 19, wherein the conductive elastomeric layer plugs the holes in the circumferential region of the elastomeric non-conductive body.

22. The balloon body of claim 19, wherein the elastomeric non-conductive body is made of silicone.

23. The balloon body of claim 19, wherein the conductive elastomeric layer is conductive silicone.

24. The balloon body of claim 19, wherein the holes are about 0.05 in. in diameter.

25. The balloon body of claim 19, wherein the elastomeric non-conductive body includes a generally "spinning top" configuration.

26. The balloon body of claim 19, wherein the elastomeric non-conductive body includes a generally funnel-shaped proximal portion and a symmetric, oppositely oriented, generally funnel-shaped distal portion connected by the circumferential region.

27. The balloon body of claim 19, wherein the circumferential region has a stepped-diameter configuration with a major-diameter central circumferential portion, a circumferential tapered portion, and a distal circumferential portion.

28. The balloon body of claim 27, wherein the one or more conductive regions is located in the major-diameter central circumferential portion.

29. The balloon body of claim 27, wherein the one or more conductive regions is located in the circumferential tapered portion.

30. The balloon body of claim 27, wherein the one or more conductive regions is located in the distal circumferential portion.

31. The balloon body of claim 19, wherein the balloon body includes one or more temperature sensors.

32. The balloon body of claim 19, further including an internal electrode located in the interior and adapted to transmit electrical current to the electrically conductive fluid medium.

33. The balloon body of claim 19, wherein the conductive elastomeric layer covers substantially all of the holes located in the circumferential region of the elastomeric non-conductive body.

34. The balloon body of claim 19, wherein the one or more conductive regions are ablative.

35. A balloon body of an electrode assembly, comprising:
    an elastomeric electrically non-conductive body expandable to a wide variety of working diameters to accommodate a wide variety of anatomical structures, the elastomeric non-conductive body including an interior adapted to receive an electrically conductive fluid medium for expanding the elastomeric non-conductive body and transmitting electrical current therethrough;
    a plurality of holes located in the elastomeric non-conductive body; and
    an electrically conductive layer covering the holes and forming one or more electrically conductive regions adapted to transmit electrical current received from the electrically conductive fluid medium through the plurality of holes to adjacent body tissue.

36. The balloon body of claim 35, wherein the conductive elastomeric layer forms multiple segmented conductive region in the shape of a ring in a circumferential region of the elastomeric non-conductive body.

37. The balloon body of claim 35, wherein the conductive elastomeric layer plugs the holes located on the elastomeric non-conductive body.

38. The balloon body of claim 35, wherein the elastomeric non-conductive body is made of silicone.

39. The balloon body of claim 35, wherein the conductive elastomeric layer is conductive silicone.

40. The balloon body of claim 35, wherein the holes are about 0.05 in. in diameter.

41. The balloon body of claim 35, wherein the balloon body includes one or more temperature sensors.

42. The balloon body of claim 35, further including an internal electrode located in the interior and adapted to transmit electrical current to the electrically conductive fluid medium.

43. The balloon body of claim 35, wherein the conductive elastomeric layer covers substantially all of the holes located on the elastomeric non-conductive body.

44. The balloon body of claim 35, wherein the one or more conductive regions are ablative.

* * * * *